United States Patent
Duis

Patent Number: 6,046,844
Date of Patent: *Apr. 4, 2000

[54] OPERATING MICROSCOPE

[75] Inventor: Wilhelm Duis, Hetlingen, Germany

[73] Assignee: J.D. Möller Optische Werke GmbH, Wedel, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/922,280

[22] Filed: Sep. 3, 1997

Related U.S. Application Data

[63] Continuation of application No. 08/627,253, Apr. 3, 1996, abandoned, which is a continuation of application No. 08/038,017, Mar. 29, 1993, abandoned.

[30] Foreign Application Priority Data

Apr. 23, 1992 [DE] Germany ............... 42 13 312

[51] Int. Cl.⁷ ............... G02B 21/26; G02B 21/00
[52] U.S. Cl. ............... 359/392; 359/368; 359/383; 250/201.3
[58] Field of Search ............... 359/368, 382, 359/383, 392, 432, 433, 694, 696; 250/201.3

[56] References Cited

U.S. PATENT DOCUMENTS

| | | | |
|---|---|---|---|
| 4,680,515 | 7/1987 | Crook | 318/254 |
| 4,930,882 | 6/1990 | Koch et al. | 359/392 |
| 4,931,630 | 6/1990 | Cohen et al. | 250/201.3 |
| 5,260,825 | 11/1993 | Nagano et al. | 250/201.3 |
| 5,557,456 | 9/1996 | Garner et al. | 359/393 |

FOREIGN PATENT DOCUMENTS

| | | | |
|---|---|---|---|
| 0119857 | 3/1984 | European Pat. Off. | 359/368 |
| 2623299 | 5/1989 | France | 359/392 |
| 221290 | 4/1985 | Germany | 359/392 |
| 3933064 | 4/1990 | Germany | 359/392 |
| 0039515 | 4/1981 | Japan | 359/368 |
| 93311 | 6/1982 | Japan | 359/392 |
| WO-94/07172 | 3/1994 | WIPO | 359/392 |

*Primary Examiner*—Thong Nguyen
*Attorney, Agent, or Firm*—Friedrich Kueffner

[57] ABSTRACT

The invention relates to an operating microscope provided with at least one motor for a magnification adjustment (zoom 1), a distance or focus adjustment (focus 6), an X adjustment or canting (7) and a Y adjustment or tilt (8), in which the zoom adjustment serves as setting signal for the focus, the X and/or the Y adjustment both as to position as well as to speed (FIG. 1).

11 Claims, 1 Drawing Sheet

OPERATING MICROSCOPE

This application is a continuation of the U.S. application, Ser. No. 08/627,253, filed on Apr. 3, 1996 which is a continuation of the U.S. application, Ser. No. 08/038,017, filed on Mar. 29, 1993, both are abandoned.

BACKGROUND OF THE INVENTION

1. Field of the Invention

The present invention relates to an operating microscope provided with at least one motor for a magnification adjustment (zoom), a distance or focus adjustment (focus), an X adjustment or canting, and a Y adjustment or tilt.

2. Description of the Related Art

In operating microscopes, following a adjustment of the tilt or canting, a correction or the focus has to be carried out in each case when the imaging object represents a surface. For microscopic viewing of different areas of a stereoscopic surface, the tilt, canting and focus will likewise have to is adjusted in order that a sharply defined image be obtained.

In order to facilitate a respective readjustment of the focal length, the canting, and the tilt of the microscope, the microscopes known in the state of the art are provided with appropriate motors or gearings. On the one hand, this has the advantage that the microscopes may also be positioned outside the work area of the operating surgeon, as on the ceiling or on a wall where they do not impede the operation to be viewed. The adjustment with the aid of servomotors does, as a rule, also requires less time and can be effected with greater accuracy. However, these adjustments also call for precise work by the microscope operator which, with a single gear stage, requires a great sensitivity. When a fine adjustment exists, a costly further gear stage is needed.

A further substantial disadvantage of existing operating microscopes is caused by the fact that operating surgeons often compelled to adapt the motor speeds manually in accordance with the respective adjusting conditions as to be able to readjust in an optimal manner. Since the selected magnification of the microscope determines the resolution and the depth of focus of the apparatus, a greater need for exact focussing exists in the smaller depth of focus ranges (higher magnifications). As a rule, this can be achieved only be carrying out the focussing at lower speeds at higher magnifications, while a higher focussing speed may be selected at lower magnification.

The selected measure of magnification determines the imaged object space so that, at a uniform given speed of adjustment, the optical image adjustment of the X motion and/or the Y motion at higher magnifications, is relatively slow and, conversely, in lower magnifications, takes place very slowly. In microscopes that have only a uniform X and/or Y adjusting speed makes finding the desired operating field more difficult. Thus, as is the case with the focussing speed, the X and Y adjusting speeds are preferably relatively high at low magnification and relatively low at high magnification.

SUMMARY OF THE INVENTION

The primary object of the present invention to improve the operating microscope to the effect that, in the case of a high magnification, a relatively low speed is automatically set for focus, cant, and tilt, and conversely, at low magnification, a relatively high speed is automatically set for focus, cant, and tilt.

In an operating microscope, according to the invention, the object is met in that the adjustment of the zoom motor serves as the setting signal for the focus, the X and the Y adjustment. The pertinent control of the operating microscope thus operates depending upon the preselected measure of magnification. From this value all the adjustments of the focal length as well as the canting or the tilt of the microscope, including the adjusting speeds, are selected.

The zoom adjustment can be measured by a sensor, be derived from the set zoom adjustment, or be extracted from a memory. In this case, the sensor may be constructed a position and/or analog speed measuring device, preferably in the form of a potentiometer, or in the form of a position and/or digital speed measuring device (pulse counting means). The digital speed measuring device may be a Hall sensor or a light barrier.

According to another embodiment of the invention, the corrective signal of the zoom motor adjustment or of the sensor, respectively, can be transmitted to a microprocessor which controls the motors or to the motors' gearing for the respective focus, the X and the Y adjustment. In each case, the microprocessor calculates, depending upon the zoom adjustment, the characteristics of the depth of focus, the X and/or the Y adjustment as well as the suitable speed of the adjustment necessary for the motors or the motors' gearing.

According to another embodiment of the invention, the instantaneous focus, X and/or Y adjustment values are supplied to an automatic controller. More particularly, to a controller which possesses a PT characteristic, in a closed control circuit. By the feedback of the instantaneous control values of the adjustment of the depth of focus as well as of the canting and the tilt, it is possible to optimize the speed of the adjustment and the adjustment accuracy.

DETAILED DESCRIPTION OF THE PREFERRED EMBODIMENT

Figure 1:
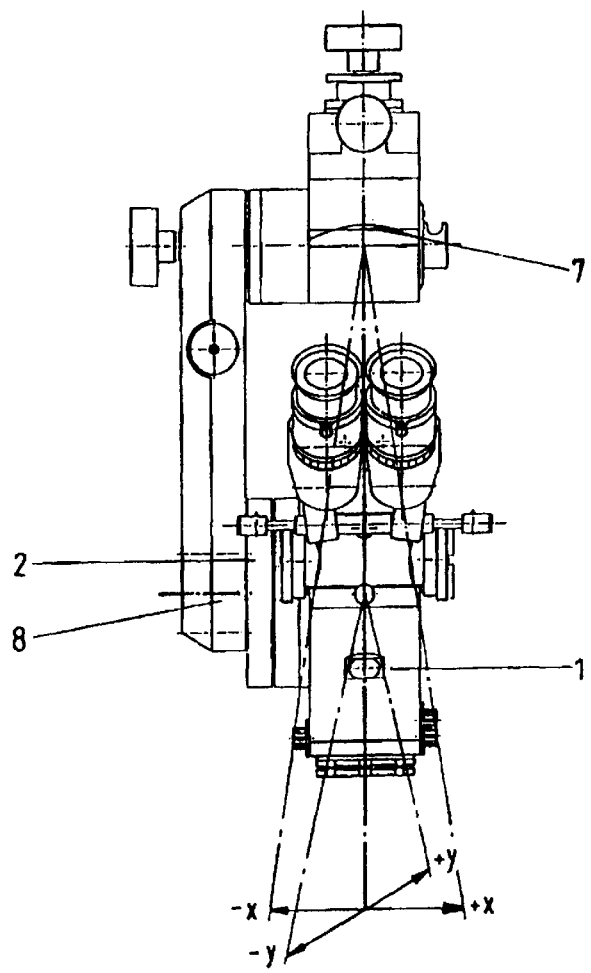
FIG. 1 is a perspective view of an operating microscope.
Figure 2:
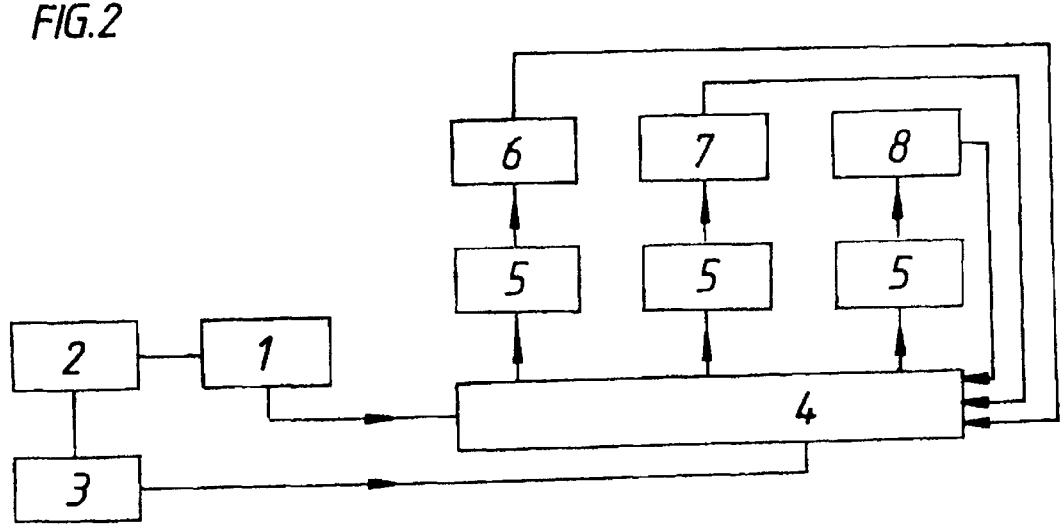
FIG. 2 is a block diagram representing the construction of the operating microscope.

Operating microscopes are generally known for their motors which are capable of fine adjustment of magnification, the definition (focus) and, the canting and the tilt. In the operating microscope depicted in FIGS. 1 and 2, the position of the zoom adjustment member 1 is measured either directly with the aid of a sensor 2. Alternatively, this measurement is extracted from a memory 3, in which the desired zoom adjustment can be stored. The sensor 2 may be an analog measuring device or a digital measuring device. For example, a simple potentiometer, a Hall sensor, or a light barrier. The adjustment signals coming from the sensor 2 or the memory 3 are transmitted to an electronic processing unit, such as a microprocessor 4, which triggers the voltage sources of the appropriate motor 5 or motor gearing, the focus 6 of the X adjustment or canting 7, and/or the Y adjustment or tilt 8. The actual values of the adjustments are supplied via respective measurement lines to the microprocessor 4 so that a closed control circuit results. A direct feedback to the microprocessor 4 takes place from the focus 6, the X adjustment or canting 7, and the Y adjustment or tilt 8 (FIG. 2).

The illustrated device function as detailed below.

It is preferred that the magnification adjustment measured by the sensor 2 is used by the microprocessor 4 for the calculation of the X, the Y, and the depth of focus adjustment. Also, the magnification adjustment value is used for the calculation of the adjustment speed tuned hereto, which is selected inversely proportional to the size of the magnification. These values are then employed such that the motors 5 are properly driven at their respective speeds and angles of rotation. The dependent zoom adjusting speeds may, according to the zoom adjustment possibilities, be adjustable continuously or within in several ranges. In addition, the microprocessor 4 controls the starting and stopping of the motor 5 according to a continuous characteristic curve which, by preference, possesses a PT behavior.

Such a control prevents jerky movements of the microscope during use. As compared to existing microscopes, this control also allows for relatively rapid adjustments that are adapted to specific magnifications.

What is claimed is:

1. An operating microscope comprising:
   a magnification adjustment means;
   a focus adjustment means;
   a canting adjustment means and a tilt adjustment means extending at a right angle to the canting adjusting means;
   a plurality of motors, each motor individually driving at an adjustment speed, the focus adjustment means, the canting adjustment means and the tilt adjustment means;
   means for producing a setting signal in dependence on an actual magnification adjustment of the magnification adjustment means; and
   means for receiving the setting signal and for producing therefrom control values for the plurality of motors for individually changing the adjustment speed of the focussing adjustment means, the canting adjustment means, and the tilt adjustment means, wherein each control value is derived from a quantity inversely proportional to the actual magnification adjustment of the magnification adjustment means.

2. The operating microscope according to claim 1, wherein the means for producing a setting signal is a sensor for measuring the actual magnification adjustment of the magnification adjustment means.

3. The operating microscope according to claim 2, wherein the sensor is a position and analog speed measurement device.

4. The operating microscope according to claim 3, wherein the sensor is a potentiometer.

5. The operating microscope according to claim 2, wherein the sensor is a position and digital speed measurement device.

6. The operating microscope according to claim 5, wherein the sensor is a pulse counting means.

7. The operating microscope according to claim 5, wherein the sensor is Hall sensor.

8. The operating microscope according to claim 5, wherein the sensor is a light barrier.

9. The operating microscope according to claim 1, wherein the means for producing a setting signal is a memory supplying magnification adjustments of the magnification adjustment means.

10. The operating microscope according to claim 1, wherein the means for receiving the setting signal and for producing control values is an electronic processing unit.

11. The operating microscope according to claim 1, wherein the control values are equivalent for the focussing adjustment means, the canting adjustment means, and the tilt adjustment means.

* * * * *